United States Patent
Kang et al.

(10) Patent No.: US 9,990,729 B2
(45) Date of Patent: Jun. 5, 2018

(54) METHODS OF AND APPARATUSES FOR MODELING STRUCTURES OF CORONARY ARTERIES FROM THREE-DIMENSIONAL (3D) COMPUTED TOMOGRAPHY ANGIOGRAPHY (CTA) IMAGES

(71) Applicant: Samsung Electronics Co., Ltd., Suwon-si, Gyeonggi-do (KR)

(72) Inventors: Dongwoo Kang, Seoul (KR); Jingu Heo, Yongin-si (KR); Seok Lee, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 292 days.

(21) Appl. No.: 14/808,399

(22) Filed: Jul. 24, 2015

(65) Prior Publication Data
US 2016/0155234 A1    Jun. 2, 2016

(30) Foreign Application Priority Data
Nov. 28, 2014    (KR) .................. 10-2014-0168326

(51) Int. Cl.
*G06T 1/00* (2006.01)
*G06T 7/00* (2017.01)
(Continued)

(52) U.S. Cl.
CPC ............ *G06T 7/0081* (2013.01); *A61B 6/032* (2013.01); *A61B 6/504* (2013.01); *A61B 6/5217* (2013.01);
(Continued)

(58) Field of Classification Search
CPC ....... A61B 6/032; A61B 6/504; A61B 6/5217; G06K 9/469; G06K 2209/05; G06T 17/00;
(Continued)

(56) References Cited

U.S. PATENT DOCUMENTS

2007/0014452 A1*  1/2007  Suresh ............... G06F 19/3437
                                                                                    382/128
2007/0225598 A1   9/2007  Buelow et al.
(Continued)

FOREIGN PATENT DOCUMENTS

KR    20130023735 A    3/2013
KR    20140071495 A    6/2014

*Primary Examiner* — Edward Park
(74) *Attorney, Agent, or Firm* — Harness, Dickey & Pierce, PLC

(57) ABSTRACT

A method of modeling a structure of a coronary artery of a subject may include: forming a learning-based shape model of the structure of the artery, based on positions of landmarks acquired from three-dimensional images; receiving a target image; and/or modeling the artery structure included in the target image, using the model. An apparatus for modeling a structure of a coronary artery may include: a memory configured to store a learning-based shape model of the artery, the learning-based shape model being formed based on positions of a plurality of landmarks acquired from three-dimensional images, the plurality of the landmarks corresponding to the artery; a communication circuit configured to receive a target image; and/or a processing circuit configured to model the artery structure included in the target image, using the model.

19 Claims, 9 Drawing Sheets

(51) Int. Cl.
*A61B 6/03* (2006.01)
*A61B 6/00* (2006.01)
*G06T 17/00* (2006.01)
*G06K 9/46* (2006.01)
*G06T 7/11* (2017.01)

(52) U.S. Cl.
CPC .............. *G06K 9/469* (2013.01); *G06T 7/11* (2017.01); *G06T 17/00* (2013.01); *G06K 2209/05* (2013.01); *G06T 2207/10081* (2013.01); *G06T 2207/20044* (2013.01); *G06T 2207/20081* (2013.01); *G06T 2207/20128* (2013.01); *G06T 2207/30101* (2013.01); *G06T 2207/30172* (2013.01); *G06T 2210/41* (2013.01)

(58) Field of Classification Search
CPC ............ G06T 7/0081; G06T 7/11; G06T 2207/10081; G06T 2207/20044; G06T 2207/20081; G06T 2207/20128; G06T 2207/30101; G06T 2207/30172; G06T 2210/41
See application file for complete search history.

(56) References Cited

U.S. PATENT DOCUMENTS

| | | | |
|---|---|---|---|
| 2008/0119734 A1 | 5/2008 | Pruvot et al. | |
| 2009/0185731 A1* | 7/2009 | Ray | G06T 7/0012 382/131 |
| 2010/0067760 A1* | 3/2010 | Zhang | G06K 9/00 382/130 |
| 2011/0026794 A1* | 2/2011 | Sundar | G06K 9/44 382/131 |
| 2011/0224542 A1 | 9/2011 | Mittal et al. | |
| 2012/0143090 A1 | 6/2012 | Hay et al. | |
| 2013/0083982 A1 | 4/2013 | Nakamura | |
| 2013/0101187 A1* | 4/2013 | Sundar | G06K 9/00362 382/128 |
| 2014/0161334 A1* | 6/2014 | Wang | G06K 9/00362 382/131 |
| 2015/0030219 A1* | 1/2015 | Madabhushi | G06T 7/0089 382/128 |
| 2015/0073262 A1* | 3/2015 | Roth | A61B 5/1077 600/411 |
| 2016/0155234 A1* | 6/2016 | Kang | G06T 7/11 345/419 |

* cited by examiner

METHODS OF AND APPARATUSES FOR MODELING STRUCTURES OF CORONARY ARTERIES FROM THREE-DIMENSIONAL (3D) COMPUTED TOMOGRAPHY ANGIOGRAPHY (CTA) IMAGES

CROSS-REFERENCE TO RELATED APPLICATION(S)

This application claims priority from Korean Patent Application No. 10-2014-0168326, filed on Nov. 28, 2014, in the Korean Intellectual Property Office (KIPO), the entire contents of which are incorporated herein by reference.

BACKGROUND

1. Field

Some example embodiments of the present disclosure may relate generally to methods for modeling structures of coronary arteries from three-dimensional (3D) computed tomography angiography (CTA) images. Some example embodiments of the present disclosure may relate generally to apparatuses for modeling structures of coronary arteries from three-dimensional (3D) computed tomography angiography (CTA) images.

2. Description of Related Art

Cardiovascular diseases may be a leading cause of death, and may cause 30% or more of all global deaths. Among people who died from cardiovascular diseases, 80% or more may die from ischemic coronary artery diseases. In medical circles, morphological features of blood vessels may be analyzed using medical images, and a presence or absence of morphological abnormalities of blood vessels, for example, a degree of angiostenosis or communication between blood vessels, may be utilized for noninvasive diagnosis and treatment.

Among medical images, coronary artery computed tomography angiography (CTA) images may be used to diagnose and treat coronary artery diseases, due to noninvasive nature, high spatial resolution, and isotropic three-dimensional (3D) features.

Medical teams may manually analyze medical images, for example, coronary artery CTA images but, accordingly, a relatively great amount of time may be required and accuracy of diagnoses may not be high.

SUMMARY

Some example embodiments may provide methods for modeling structures of coronary arteries.

Some example embodiments may provide apparatuses for modeling structures of coronary arteries.

In some example embodiments, a method of modeling a structure of a coronary artery of a subject may comprise: forming a learning-based shape model of the structure of the coronary artery, based on positions of a plurality of landmarks acquired from each of a plurality of three-dimensional (3D) images; receiving a target image; modeling the structure of the coronary artery included in the target image, using the learning-based shape model; and/or analyzing the modeled structure of the coronary artery to assist in diagnosis, treatment, or diagnosis and treatment of the subject.

In some example embodiments, the modeling of the structure may comprise: acquiring positions of points representing the coronary artery from the target image, based on the learning-based shape model; acquiring a centerline of the coronary artery from the target image based on the positions of the points; and/or modeling the structure of the coronary artery, using the positions of the points and the centerline.

In some example embodiments, the acquiring of the positions of the points may comprise: setting initial positions of the points, based on a mean shape of the learning-based shape model; changing the initial positions based on energy difference between the mean shape and a shape formed by the points; and/or acquiring the positions of the points based on the changed initial positions.

In some example embodiments, the acquiring of the centerline may comprise: acquiring the centerline using a local-segmentation scheme and a thinning scheme.

In some example embodiments, the acquiring of the centerline may comprise: segmenting a lumen of the coronary artery for each of the positions of the points in the target image, using a region-growing scheme or a graph-cut scheme; and/or acquiring a centerline of the segmented lumen by applying the thinning scheme to the segmented lumen.

In some example embodiments, the segmenting of the lumen may comprise: scanning intensities of neighboring pixels within a distance from each of the positions of the points in the target image; setting the intensities as stopping condition pixel values required for the region-growing scheme; and/or segmenting the lumen based on the stopping condition pixel values.

In some example embodiments, the segmenting of the lumen may comprise: setting the points in the target image as first seed points required for the graph-cut scheme, and setting, as second seed points, neighboring points each having an intensity equal to or less than 0 Hounsfield units (HU) among the neighboring points adjacent to the points in the target image; and/or segmenting the lumen based on the first seed points and the second seed points.

In some example embodiments, the method may further comprise: acquiring the centerline by connecting centerlines of the segmented lumen.

In some example embodiments, the forming of the learning-based shape model may comprise: forming an active shape model (ASM) or an active appearance model (AAM) of the coronary artery, based on the positions of the plurality of the landmarks.

In some example embodiments, the forming of the learning-based shape model may comprise: acquiring the positions of the plurality of the landmarks corresponding to the coronary artery from each of the 3D images; and/or calculating a main variation and a mean shape of the coronary artery based on the positions of the plurality of the landmarks.

In some example embodiments, a non-transitory computer-readable medium may comprise program code that, when executed by a processor, performs functions according to a method of modeling a structure of a coronary artery may comprise: forming a learning-based shape model of the structure of the coronary artery, based on positions of a plurality of landmarks acquired from each of a plurality of three-dimensional (3D) images; receiving a target image; and/or modeling the structure of the coronary artery included in the target image, using the learning-based shape model.

In some example embodiments, an apparatus for modeling a structure of a coronary artery may comprise: a memory configured to store a learning-based shape model of the coronary artery, the learning-based shape model being formed based on positions of a plurality of landmarks acquired from each of a plurality of three-dimensional (3D) images, the plurality of the landmarks corresponding to the coronary artery; a communication circuit configured to receive a target image; and/or a processing circuit configured to model the structure of the coronary artery included in the target image, using the learning-based shape model.

In some example embodiments, the processor may comprise: a first acquisition circuit configured to acquire positions of points representing the coronary artery from the target image, based on the learning-based shape model; a second acquisition circuit configured to acquire a centerline of the coronary artery from the target image, based on the positions of the points; and/or a modeling circuit configured to model the structure of the coronary artery, using the positions of the points and the centerline.

In some example embodiments, the first acquisition circuit may be further configured to set initial positions of the points, based on a mean shape of the learning-based shape model, to change the initial positions based on energy difference between the mean shape and a shape formed by the points, and to acquire the positions of the points based on the changed initial positions.

In some example embodiments, the second acquisition circuit may be further configured to acquire the centerline using a local-segmentation scheme and a thinning scheme.

In some example embodiments, the second acquisition circuit may be further configured to segment a lumen of the coronary artery for each of the positions of the points in the target image, using a region-growing scheme or a graph-cut scheme, and to acquire a centerline of the segmented lumen by applying the thinning scheme to the segmented lumen.

In some example embodiments, the second acquisition circuit may be further configured to scan intensities of neighboring pixels within a distance from each of the positions of the points, to set the intensities as stopping condition pixel values required for the region-growing scheme, and to segment the lumen based on the stopping condition pixel values.

In some example embodiments, the second acquisition circuit may be further configured to set the points as first seed points required for the graph-cut scheme, to set, as second seed points, neighboring points each having an intensity equal to or less than 0 Hounsfield units (HU) among the neighboring points adjacent to the points in the target image, and to segment the lumen based on the first seed points and the second seed points.

In some example embodiments, the second acquisition circuit may be further configured to acquire the centerline by connecting centerlines of the segmented lumen.

In some example embodiments, the apparatus may further comprise: a generating circuit configured to calculate a main variation and a mean shape of the coronary artery in the 3D images by applying a principal component analysis (PCA) scheme to the positions of the plurality of the landmarks.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
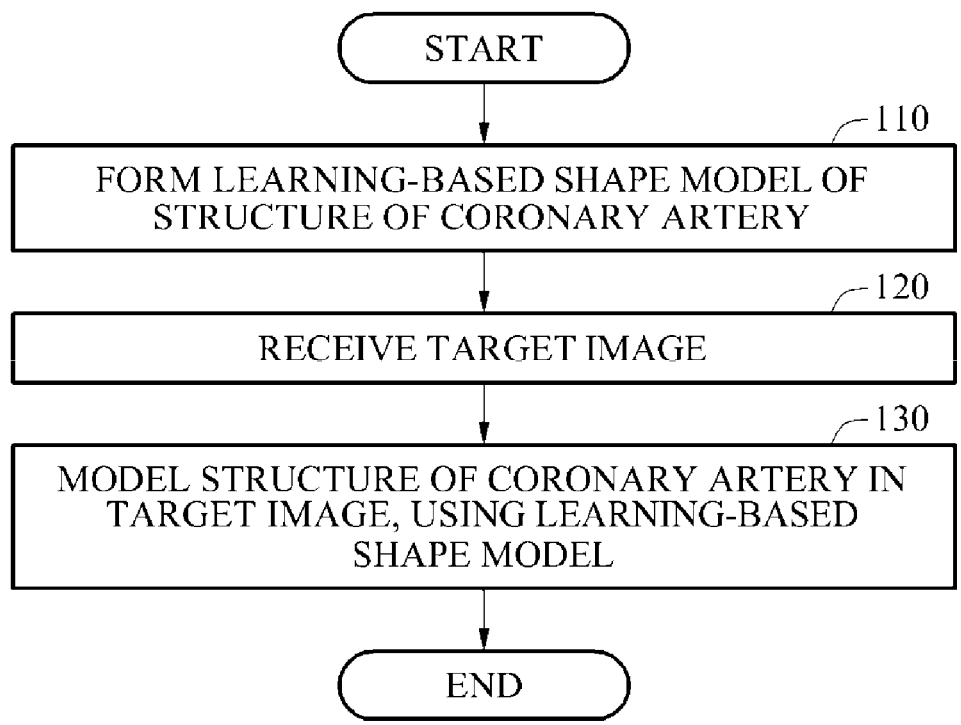
FIG. 1 is a flowchart illustrating a method of modeling a structure of a coronary artery according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

FIG. 1 is a flowchart illustrating a method of modeling a structure of a coronary artery according to some example embodiments.

Referring to FIG. 1, in operation 110, an apparatus for modeling a coronary artery (hereinafter, referred to as a "modeling apparatus") according to some example embodiments may form a learning-based shape model of a structure of a coronary artery based on positions of landmarks acquired from each of a plurality of three-dimensional (3D) computed tomography angiography (CTA) images. The learning-based shape model formed in operation 110 may be stored in a memory in the form of a database or the like. The learning-based shape model may be, for example, an active shape model (ASM), or an active appearance model (AAM).

A method by which the modeling apparatus forms the learning-based shape model will be further described with reference to FIGS. 2 and 3.

In operation 120, the modeling apparatus may receive a target image.

In operation 130, the modeling apparatus may model a structure of a coronary artery included in the target image received in operation 120, using the learning-based shape model formed in operation 110. The structure of the coronary artery may be understood to refer to all of centerlines connecting points in addition to a start point, an end point, and branch points of the coronary artery.

In some example embodiments, the method may further comprise analyzing the modeled structure of the coronary artery to assist in diagnosis, treatment, or diagnosis and treatment of the subject.

In some example embodiments, the model of the structure of the coronary artery may be output to a display device. The displayed model may be analyzed, for example, by medical personnel.

In some example embodiments, the model of the structure of the coronary artery may be stored for future reference or analysis. The storage may be, for example, to a database of models of the same coronary artery or to a database of models of other coronary arteries.

In some example embodiments, the model of the structure of the coronary artery may be analyzed by a computer program based on, for example, comparison of the model to previous models of the same coronary artery or to models of other coronary arteries from a database.

In some example embodiments, the analysis by computer program may be compared to the analysis by medical personnel, for example, to improve accuracy and completeness of the analysis.

A method by which the modeling apparatus models the structure of the coronary artery in the target image will be further described with reference to FIGS. 4 through 7.

Figure 2:
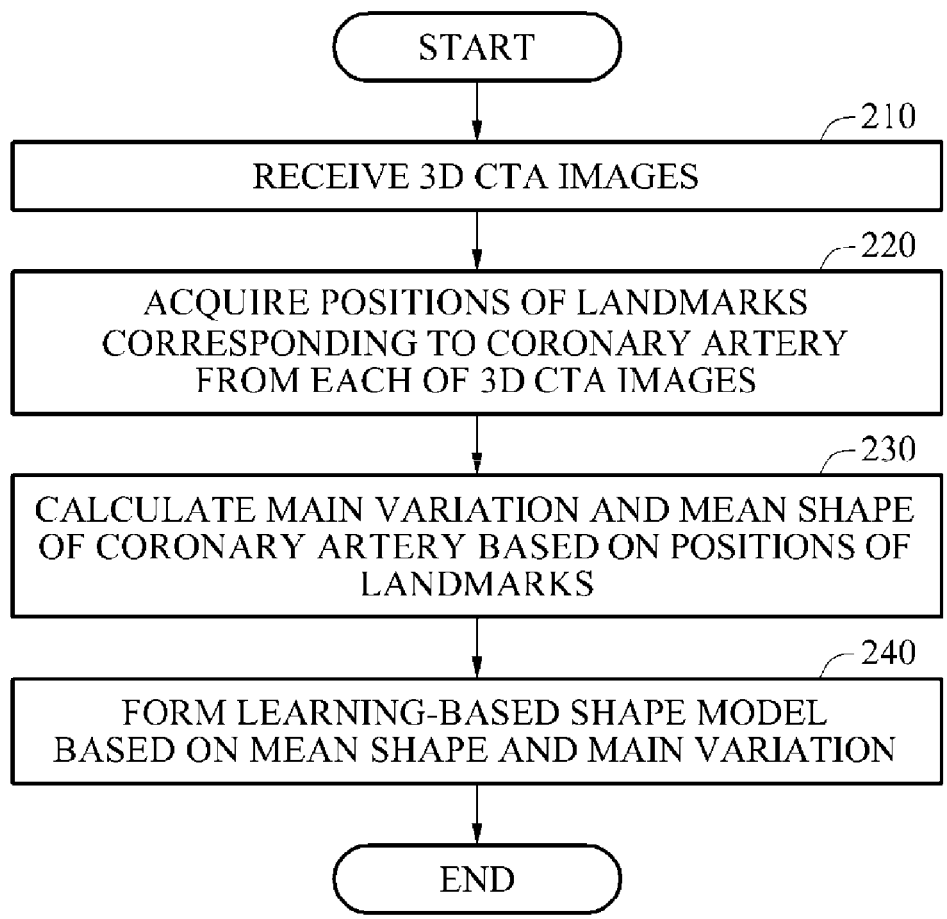
FIG. 2 is a flowchart illustrating a method of forming a learning-based shape model according to some example embodiments.

FIG. 2 is a flowchart illustrating a method of forming a learning-based shape model according to some example embodiments.

Referring to FIG. 2, in operation 210, a modeling apparatus according to some example embodiments may receive a plurality of 3D CTA images.

In operation 220, the modeling apparatus may acquire positions of a plurality of landmarks corresponding to a coronary artery from each of the 3D CTA images.

In operation 230, the modeling apparatus may calculate a main variation and a mean shape of the coronary artery, based on the positions of the landmarks acquired in operation 220. For example, the modeling apparatus may apply a principal component analysis (PCA) scheme to the positions of the landmarks, and may calculate the main variation and the mean shape of the coronary artery.

In operation 240, the modeling apparatus may form the learning-based shape model, based on the mean shape and the main variation calculated in operation 230. The formed shape model may have, for example, the same shape as a shape of a shape model 310 of FIG. 3.

In some example embodiments, the main variation, the mean shape, or the main variation and the mean shape of the coronary artery may be stored for future reference or analysis. The storage may be, for example, to a database of models of the same coronary artery or to a database of models of other coronary arteries.

Figure 3:
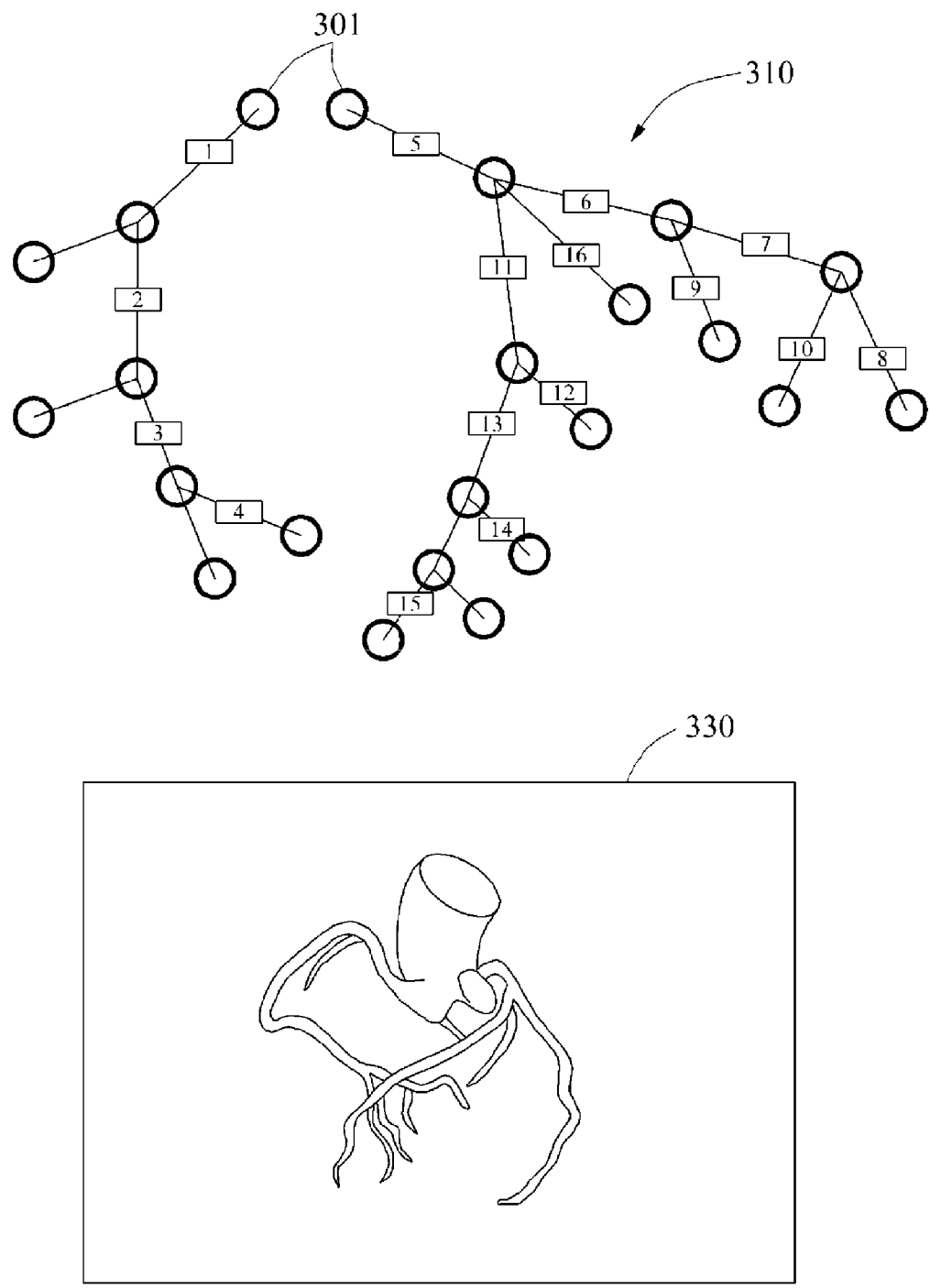
FIG. 3 illustrates a learning-based shape model according to some example embodiments.

FIG. 3 illustrates a learning-based shape model according to some example embodiments.

Referring to FIG. 3, the shape model 310 may represent a generalized structure of a coronary artery.

The shape model 310 may be acquired from a 3D CTA image 330 through learning.

A structure of a coronary artery may be obtained by analyzing a structure of a standard American Heart Association (AHA) 17-segment model of a coronary artery in the 3D CTA image 330. The structure of the standard AHA 17-segment model may be analyzed by positions of 23 points in total including a start point, an end point, and branch points. The 23 points may be referred to as landmarks 301.

To form the shape model 310, positions of landmarks 301 corresponding to a coronary artery may be acquired from each of 100 3D CTA images 330 of patients. In some example embodiments, the positions of the landmarks 301 may be manually acquired or acquired by a desired algorithm (that may or may not be predetermined). The positions of the landmarks 301 may be manually designated to be in a center of a lumen of the coronary artery, and may be learned.

In the structure of the coronary artery, the landmarks 301 may have unique numbers, for example, numbers 1 through 23.

The shape model 310 may be formed based on a main variation and a mean shape of the coronary artery calculated by applying a PCA scheme to positions of the landmarks 301.

Figure 4:
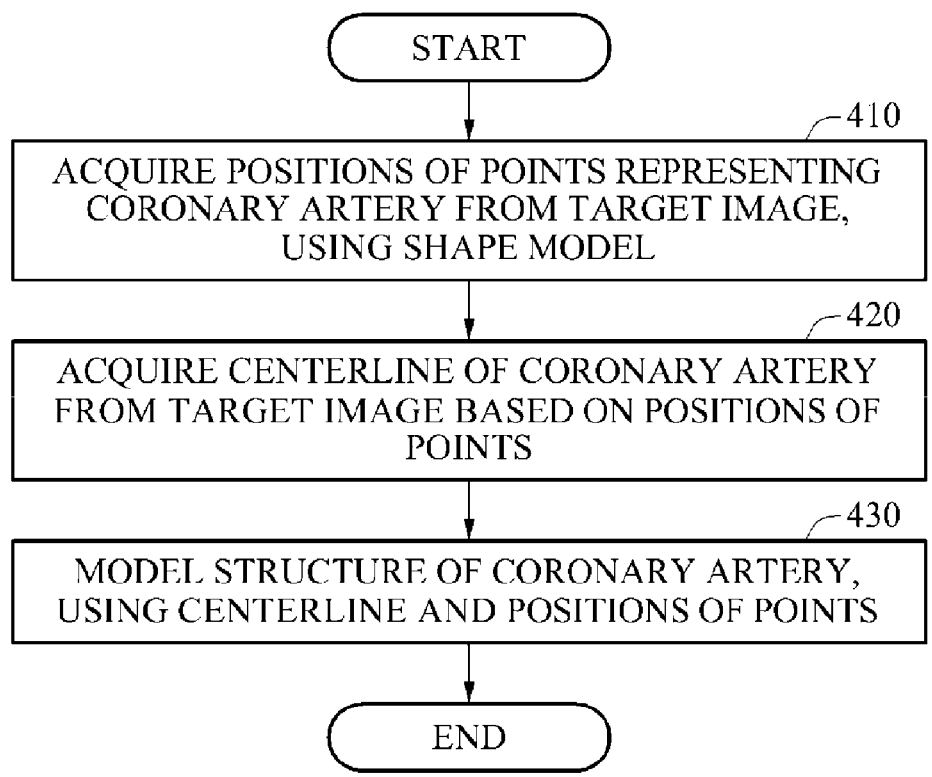
FIG. 4 is a flowchart illustrating a method of modeling a structure of a coronary artery according to some example embodiments.

FIG. 4 is a flowchart illustrating a method of modeling a structure of a coronary artery according to some example embodiments.

Referring to FIG. 4, in operation 410, a modeling apparatus according to some example embodiments may acquire positions of points representing the coronary artery from a target image, using a shape model. A method by which the modeling apparatus acquires the positions of the points will be further described with reference to FIG. 5.

In operation 420, the modeling apparatus may acquire a centerline of the coronary artery from the target image, based on the positions of the points acquired in operation 410. The modeling apparatus may acquire the centerline, using a local-segmentation scheme and a thinning scheme. A method by which the modeling apparatus acquires the centerline will be further described with reference to FIGS. 7 and 8.

In operation 430, the modeling apparatus may model the structure of the coronary artery, based on the positions of the points acquired in operation 410 and the centerline acquired in operation 420. For example, the modeling apparatus may fully represent a structure of a coronary artery included in the target image, based on the points and the centerline.

Figure 5:
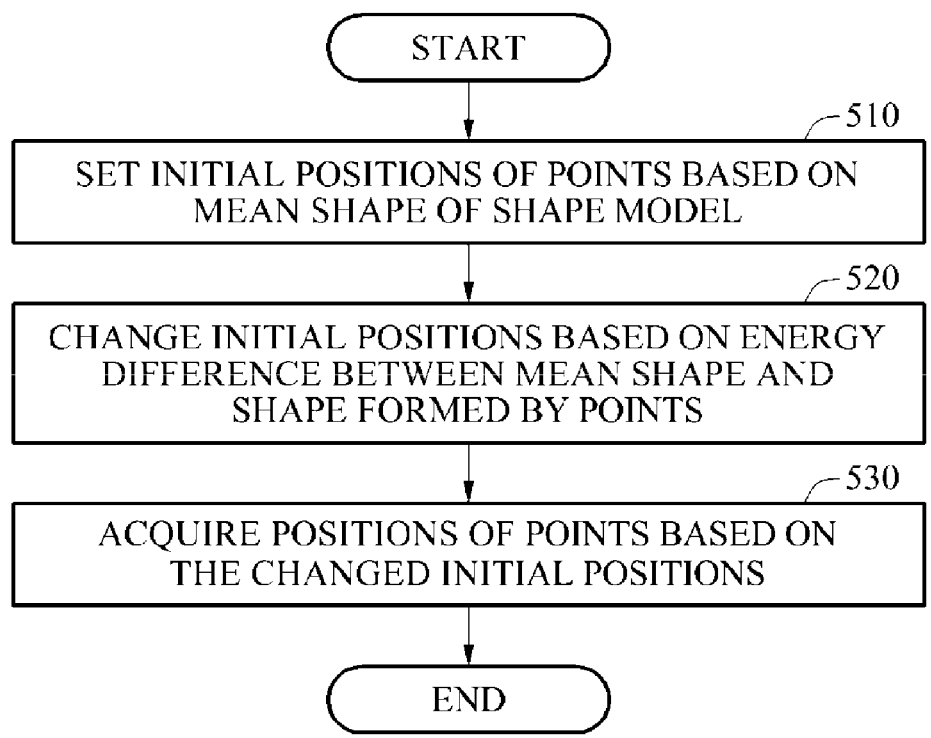
FIG. 5 is a flowchart illustrating a method of acquiring positions of points representing a coronary artery from a target image according to some example embodiments.

FIG. 5 is a flowchart illustrating a method of acquiring positions of points representing a coronary artery from a target image according to some example embodiments.

Referring to FIG. 5, in operation 510, a modeling apparatus according to some example embodiments may set initial positions of points, based on a mean shape of a shape model. For example, the modeling apparatus may set initial positions of the points to be located in the target image, based on a generalized structure of the coronary artery, that is, the mean shape of the shape model.

In operation 520, the modeling apparatus may change the initial positions, based on an energy difference between the mean shape and a shape formed by the points. For example, the initial positions may be changed as shown in FIG. 6.

In operation 530, the modeling apparatus may acquire positions of the points based on the initial positions changed in operation 520. The modeling apparatus may acquire the initial positions changed in operation 520 as final positions of the points.

Figure 6:
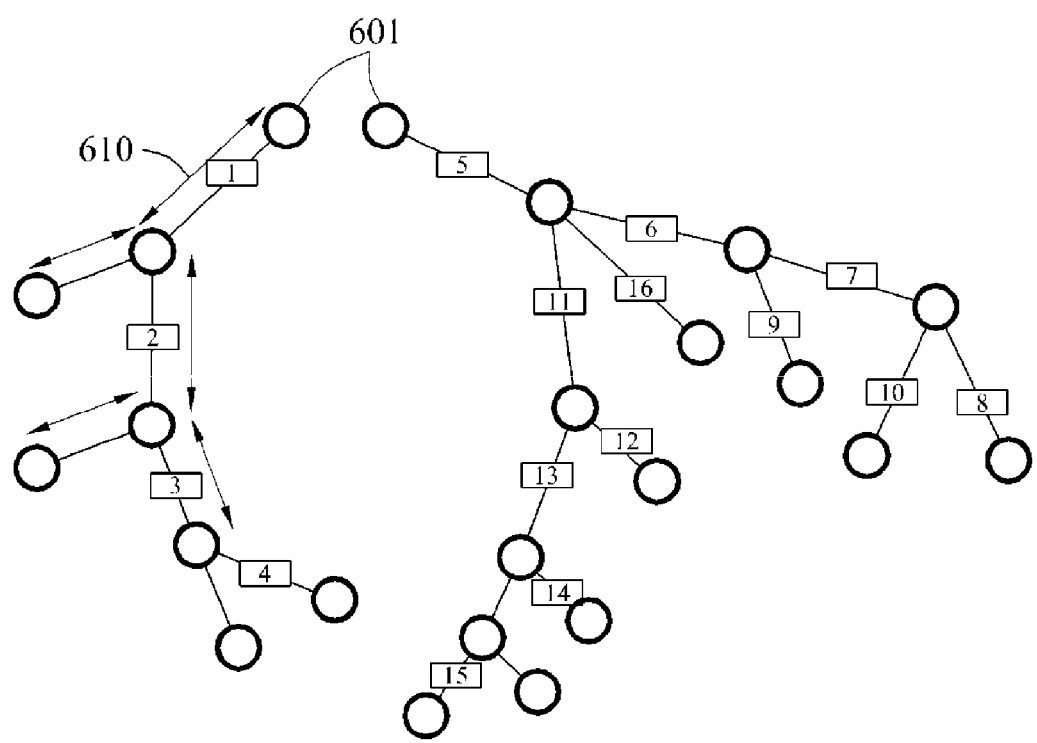
FIG. 6 illustrates a change in positions of points representing a coronary artery in a target image according to some example embodiments.

FIG. 6 illustrates a change in positions of points representing a coronary artery in a target image according to some example embodiments.

Referring to FIG. 6, a modeling apparatus according to some example embodiments may change initial positions of points 601.

The modeling apparatus may change initial positions of points, for example, using an energy function. For example, the modeling apparatus may change initial positions of points, by adjusting a distance 610 between the points so that an energy difference between a mean shape and a shape formed by the points may be minimized. The energy difference may be, for example, a Mahalanobis distance or the like.

Figure 7:
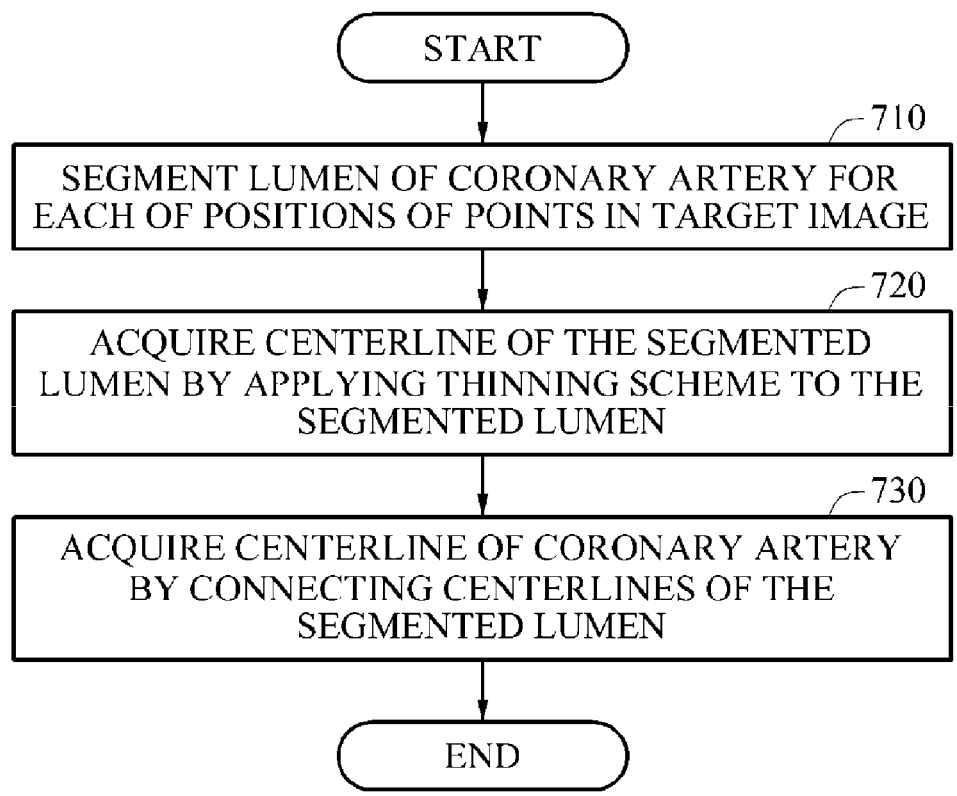
FIG. 7 is a flowchart illustrating a method of acquiring a centerline of a coronary artery from a target image according to some example embodiments.

FIG. 7 is a flowchart illustrating a method of acquiring a centerline of a coronary artery from a target image according to some example embodiments.

Referring to FIG. 7, in operation 710, a modeling apparatus according to some example embodiments may segment a lumen of the coronary artery for each of positions of points in the target image.

For example, the modeling apparatus may sequentially perform a local-segmentation of lumens between points of a coronary artery, for example, between points 1 and 2, between points 2 and 3, and between points 3 and 4, for each of positions of points in the target image.

In some example embodiments, the modeling apparatus may use a region-growing scheme or a graph-cut scheme to segment the lumen of the coronary artery.

In some example embodiments, the modeling apparatus may use the region-growing scheme to segment the lumen.

The region-growing scheme may require a stopping condition pixel value in an algorithm. To obtain the stopping condition pixel value, neighboring pixel intensities of neighboring pixels around points may be scanned and used.

The modeling apparatus may scan an intensity of a neighboring pixel within a desired distance (that may or may not be predetermined) (for example, 1 millimeter (mm)) from a position of each of the points. The modeling apparatus may set the intensity as a stopping condition pixel value required for the region-growing scheme. The modeling apparatus may segment the lumen based on the stopping condition pixel value.

In some example embodiments, the modeling apparatus may use the graph-cut scheme to segment the lumen.

The modeling apparatus may set acquired points as first seed points for an object (for example, a coronary artery). Also, the modeling apparatus may set, as second seed points for a background, neighboring points each having an intensity equal to or less than 0 Hounsfield units (HU) among neighboring points adjacent to the acquired points. In some example embodiments, HU may represent a unit of a pixel intensity of a CTA image.

The modeling apparatus may segment the lumen, based on the first seed points and the second seed points.

In operation 720, the modeling apparatus may acquire a centerline of the lumen segmented in operation 710 by applying a thinning scheme to the segmented lumen.

The thinning scheme may be one of morphological operations used to remove selected foreground pixels from binary images, like erosion or opening. The thinning scheme may be generally used for skeletonization by tidying up an edge detection result by reducing all lines to a single pixel thickness.

For example, the modeling apparatus may apply the thinning scheme to a segmented lumen of a coronary artery, and may acquire a centerline of the coronary artery in which an actual shape of the lumen (for example, bent lumen or curved lumen) is skeletonized.

Figure 8:
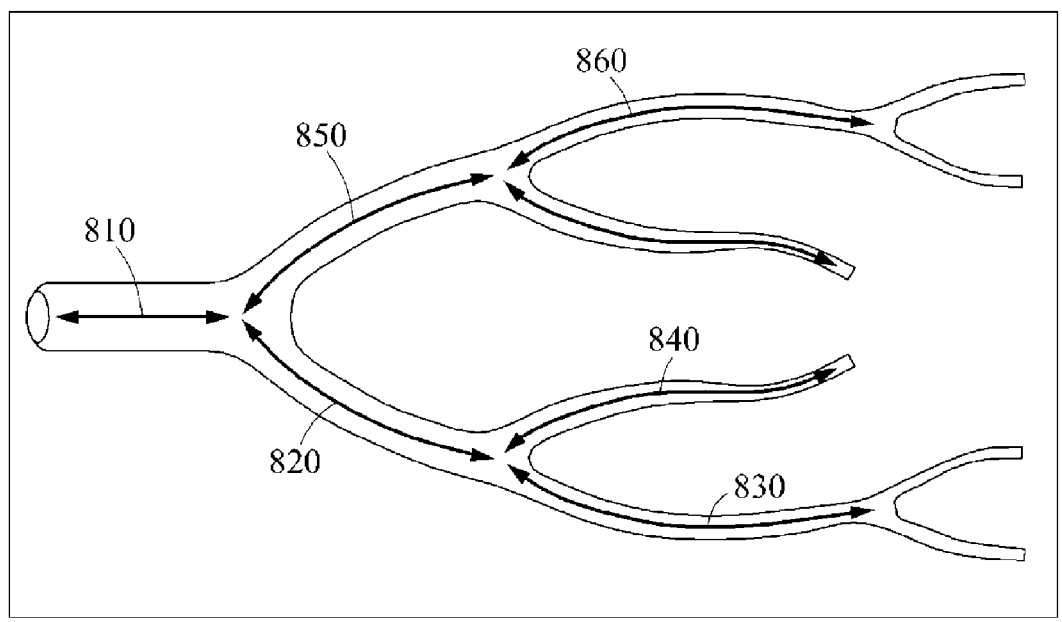
FIG. 8 illustrates a method of acquiring a centerline of a coronary artery according to some example embodiments.

In operation 730, the modeling apparatus may acquire the centerline of the coronary artery by connecting centerlines of the segmented lumen, as shown in FIG. 8.

The modeling apparatus according to some example embodiments may store a segmentation result of the coronary artery segmented in operation 710, and may use the stored segmentation result again to segment a modeled portion of the coronary artery.

FIG. 8 illustrates a method of acquiring a centerline of a coronary artery according to some example embodiments.

Referring to FIG. 8, local centerlines 810, 820, 830, 840, 850, and 860 of a coronary artery may be segmented from a CTA image.

A modeling apparatus according to some example embodiments may obtain a single line by applying the above-described thinning scheme to a lumen of a coronary artery segmented for each of positions of points. The line may be the local centerlines 810 through 860 connecting the points.

The modeling apparatus may connect all the local centerlines 810 through 860, and may acquire a composite centerline connecting a start point to an end point of the coronary artery.

Figure 9:
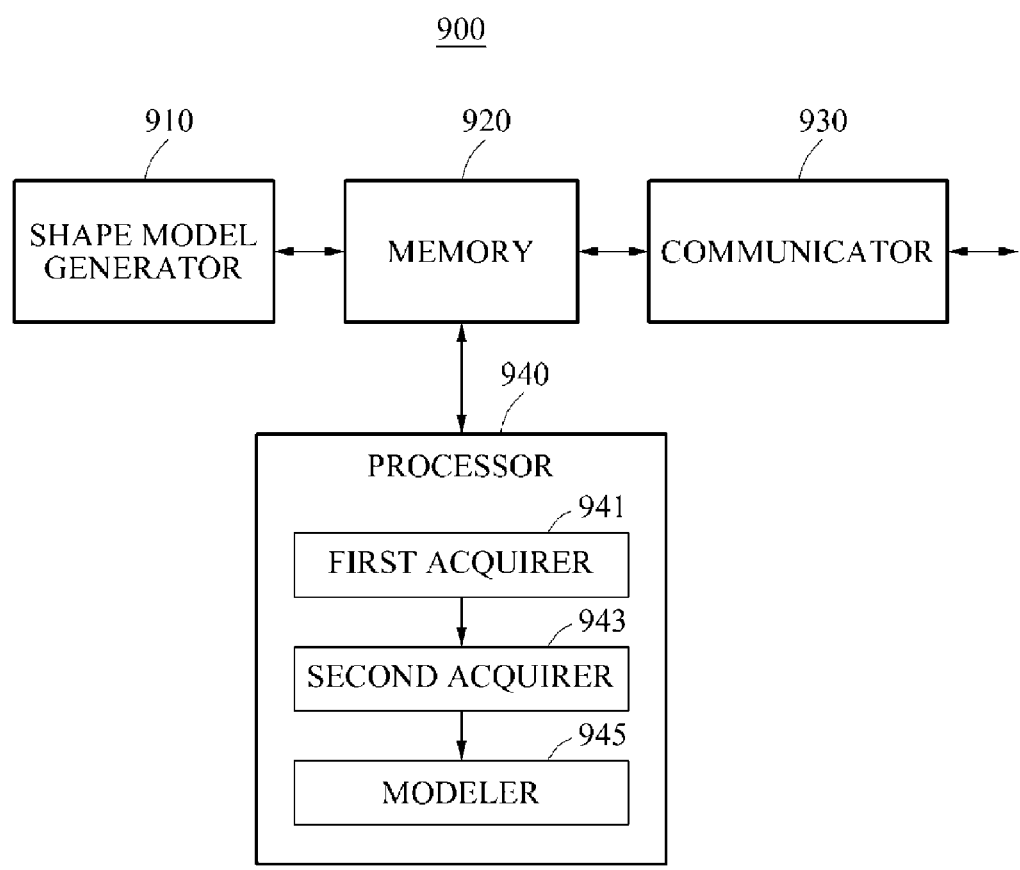
FIG. 9 is a block diagram illustrating an apparatus for modeling a structure of a coronary artery according to some example embodiments.

FIG. 9 is a block diagram illustrating a modeling apparatus 900 for modeling a structure of a coronary artery according to some example embodiments.

Referring to FIG. 9, the modeling apparatus 900 may include a shape model generator 910 (e.g., generating circuit), a memory 920, a communicator 930 (e.g., communication circuit), and a processor 940 (e.g., processing circuit).

The shape model generator 910 may calculate a main variation and a mean shape of a coronary artery, based on positions of a plurality of landmarks corresponding to the coronary artery. The positions of the landmarks may be acquired from each of a plurality of 3D CTA images. The 3D images may be, for example, 3D CTA images of objects.

The shape model generator 910 may calculate the main variation and the mean shape in the 3D images by applying, for example, a PCA scheme to the positions of the landmarks, and may generate a learning-based shape model of the coronary artery.

The memory 920 may store the learning-based shape model generated by the shape model generator 910, for example, in the form of a database. The learning-based shape model may be formed based on the positions of the landmarks acquired from each of the 3D images.

The communicator 930 may receive a target image. The target image may be a 3D CTA image of an object (for example, a patient) of which a structure of a coronary artery is to be analyzed.

The processor 940 may model a structure of a coronary artery in the target image, using the learning-based shape model.

The processor 940 may include a first acquirer 941 (e.g., first acquisition circuit), a second acquirer 943 (e.g., second acquisition circuit), and a modeler 945 (e.g., modeling circuit).

The first acquirer 941 may acquire positions of points representing the coronary artery from the target image, using the learning-based shape model.

The first acquirer 941 may set initial positions of the points based on a mean shape of the learning-based shape model, and may change the initial positions based on an energy difference between the mean shape and a shape formed by the points. For example, the first acquirer 941 may change the initial positions so that the energy difference may be minimized, using an energy minimization function.

The first acquirer 941 may acquire the positions of the points based on the changed initial positions.

The second acquirer 943 may acquire a centerline of the coronary artery from the target image, based on the positions of the points acquired by the first acquirer 941.

To acquire the centerline, the second acquirer 943 may use a local-segmentation scheme and a thinning scheme.

The second acquirer 943 may segment a lumen of the coronary artery for each of the positions of the points in the target image, using a region-growing scheme or a graph-cut scheme. The second acquirer 943 may acquire a centerline of the segmented lumen by applying the thinning scheme to the segmented lumen.

The region-growing scheme or the graph-cut scheme may be included in the local-segmentation scheme.

In some example embodiments, the second acquirer 943 may use the region-growing scheme to segment the lumen.

In some example embodiments, the second acquirer 943 may scan intensities of neighboring pixels within a desired distance (that may or may not be predetermined) from the positions of the points acquired by the first acquirer 941, and may set the intensities as stopping condition pixel values required for the region-growing scheme. The second acquirer 943 may segment the lumen based on the stopping condition pixel values.

In some example embodiments, the second acquirer 943 may use the graph-cut scheme to segment the lumen.

In some example embodiments, the second acquirer 943 may set the points as first seed points required for the graph-cut scheme, and may set, as second seed points, neighboring points each having an intensity equal to or less than 0 HU among neighboring points adjacent to the points.

The second acquirer 943 may segment the lumen based on the first seed points and the second seed points.

The second acquirer 943 may acquire the centerline of the coronary artery by connecting centerlines of the segmented lumen.

The modeler 945 may model the structure of the coronary artery, based on the positions of the points acquired by the first acquirer 941 and the centerline acquired by the second acquirer 943.

The units and/or modules described herein may be implemented using hardware components, software components, or a combination thereof. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

The algorithms discussed in this application (e.g., for modeling structures of coronary arteries) may be used in more general purpose apparatuses and/or methods for modeling. For example, the algorithms may be used for more general principal component analysis schemes, more general analysis schemes, and for modeling more general structures.

The methods described above may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' may be interpreted as software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiment, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to methods and apparatuses in the medical field, those skilled in the art will appreciate that some example embodiments may be applied to other types of methods and apparatuses, such as methods and apparatuses not in the medical field (e.g., methods and apparatuses in the chemical field, methods and apparatuses in the military field, methods and apparatuses in the security field, or more general purpose methods and apparatuses. Those skilled in the art will appreciate that the methods and apparatuses described in this application have a myriad of practical uses.

Although some example embodiments of the present disclosure have been shown and described, it would be appreciated by those skilled in the art that changes may be made in these example embodiments without departing from the principles and spirit of the invention, the scope of which is defined in the claims and their equivalents.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A method of modeling a structure of a coronary artery of a subject, the method comprising:
forming a learning-based shape model of the structure of the coronary artery, based on positions of a plurality of landmarks acquired from each of a plurality of three-dimensional (3D) images;
receiving a target image; and
modeling the structure of the coronary artery included in the target image, using the learning-based shape model, wherein the modeling of the structure includes
acquiring positions of points representing the coronary artery from the target image, based on the learning-based shape model,
acquiring a centerline of the coronary artery from the target image based on the positions of the points, and
modeling the structure of the coronary artery, using the positions of the points and the centerline.

2. The method of claim 1, wherein the acquiring of the positions of the points comprises:
setting initial positions of the points, based on a mean shape of the learning-based shape model;
changing the initial positions based on energy difference between the mean shape and a shape formed by the points; and
acquiring the positions of the points based on the changed initial positions.

3. The method of claim 1, wherein the acquiring of the centerline comprises:
acquiring the centerline using a local-segmentation scheme and a thinning scheme.

4. The method of claim 3, wherein the acquiring of the centerline comprises:
segmenting a lumen of the coronary artery for each of the positions of the points in the target image, using a region-growing scheme or a graph-cut scheme; and
acquiring a centerline of the segmented lumen by applying the thinning scheme to the segmented lumen.

5. The method of claim 4, wherein the segmenting of the lumen comprises:
scanning intensities of neighboring pixels within a distance from each of the positions of the points in the target image;
setting the intensities as stopping condition pixel values required for the region-growing scheme; and
segmenting the lumen based on the stopping condition pixel values.

6. The method of claim 4, wherein the segmenting of the lumen comprises:
setting the points in the target image as first seed points required for the graph-cut scheme, and setting, as second seed points, neighboring points each having an intensity equal to or less than 0 Hounsfield units (HU) among the neighboring points adjacent to the points in the target image; and
segmenting the lumen based on the first seed points and the second seed points.

7. The method of claim 4, further comprising:
acquiring the centerline by connecting centerlines of the segmented lumen.

8. The method of claim 1, wherein the forming of the learning-based shape model comprises:
forming an active shape model (ASM) or an active appearance model (AAM) of the coronary artery, based on the positions of the plurality of the landmarks.

9. The method of claim 1, wherein the forming of the learning-based shape model comprises:
acquiring the positions of the plurality of the landmarks corresponding to the coronary artery from each of the 3D images; and
calculating a main variation and a mean shape of the coronary artery based on the positions of the plurality of the landmarks.

10. A non-transitory computer-readable medium comprising program code that, when executed by a processor, performs functions according to the method of claim 1.

11. The method of claim 1, further comprising:
analyzing the modeled structure of the coronary artery to assist in diagnosis, treatment, or diagnosis and treatment of the subject.

12. An apparatus for modeling a structure of a coronary artery, the apparatus comprising:
a memory configured to store a learning-based shape model of the coronary artery, the learning-based shape model being formed based on positions of a plurality of landmarks acquired from each of a plurality of three-dimensional (3D) images, the plurality of the landmarks corresponding to the coronary artery;
a communication circuit configured to receive a target image; and
a processing circuit configured to model the structure of the coronary artery included in the target image, using the learning-based shape model,
wherein the processing circuit includes
a first acquisition circuit configured to acquire positions of points representing the coronary artery from the target image, based on the learning-based shape model,
a second acquisition circuit configured to acquire a centerline of the coronary artery from the target image, based on the positions of the points, and
a modeling circuit configured to model the structure of the coronary artery, using the positions of the points and the centerline.

13. The apparatus of claim 12, wherein the first acquisition circuit is further configured to set initial positions of the points, based on a mean shape of the learning-based shape model, to change the initial positions based on energy difference between the mean shape and a shape formed by the points, and to acquire the positions of the points based on the changed initial positions.

14. The apparatus of claim 12, wherein the second acquisition circuit is further configured to acquire the centerline using a local-segmentation scheme and a thinning scheme.

15. The apparatus of claim 14, wherein the second acquisition circuit is further configured to segment a lumen of the coronary artery for each of the positions of the points in the target image, using a region-growing scheme or a graph-cut scheme, and to acquire a centerline of the segmented lumen by applying the thinning scheme to the segmented lumen.

16. The apparatus of claim 15, wherein the second acquisition circuit is further configured to scan intensities of neighboring pixels within a distance from each of the positions of the points, to set the intensities as stopping condition pixel values required for the region-growing scheme, and to segment the lumen based on the stopping condition pixel values.

17. The apparatus of claim 15, wherein the second acquisition circuit is further configured to set the points as first seed points required for the graph-cut scheme, to set, as second seed points, neighboring points each having an intensity equal to or less than 0 Hounsfield units (HU) among the neighboring points adjacent to the points in the target image, and to segment the lumen based on the first seed points and the second seed points.

18. The apparatus of claim 15, wherein the second acquisition circuit is further configured to acquire the centerline by connecting centerlines of the segmented lumen.

19. The apparatus of claim 12, further comprising:
a generating circuit configured to calculate a main variation and a mean shape of the coronary artery in the 3D images by applying a principal component analysis (PCA) scheme to the positions of the plurality of the landmarks.

* * * * *